(12) United States Patent
Soon-Shiong

(10) Patent No.: US 12,043,656 B2
(45) Date of Patent: Jul. 23, 2024

(54) ADVANCED AVATAR DENDRITIC CELLS

(71) Applicant: ImmunityBio, Inc., Culver City, CA (US)

(72) Inventor: Patrick Soon-Shiong, Culver City, CA (US)

(73) Assignee: ImmunityBio, Inc., Culver City, CA (US)

( * ) Notice: Subject to any disclaimer, the term of this patent is extended or adjusted under 35 U.S.C. 154(b) by 412 days.

(21) Appl. No.: 17/588,949

(22) Filed: Jan. 31, 2022

(65) Prior Publication Data

US 2022/0153811 A1 May 19, 2022

Related U.S. Application Data

(62) Division of application No. 17/041,377, filed as application No. PCT/US2019/025581 on Apr. 3, 2019, now Pat. No. 11,267,866.

(60) Provisional application No. 62/652,554, filed on Apr. 4, 2018.

(51) Int. Cl.
| | |
|---|---|
| C07K 14/715 | (2006.01) |
| A61K 38/17 | (2006.01) |
| A61K 38/19 | (2006.01) |
| A61K 38/20 | (2006.01) |
| A61K 45/06 | (2006.01) |
| C07K 14/52 | (2006.01) |
| C07K 14/54 | (2006.01) |
| C07K 14/71 | (2006.01) |

(52) U.S. Cl.
CPC ........ *C07K 14/7155* (2013.01); *A61K 38/179* (2013.01); *A61K 38/1793* (2013.01); *A61K 38/195* (2013.01); *A61K 38/2086* (2013.01); *A61K 45/06* (2013.01); *C07K 14/521* (2013.01); *C07K 14/5443* (2013.01); *C07K 14/71* (2013.01); *C07K 2319/30* (2013.01); *C07K 2319/31* (2013.01)

(58) Field of Classification Search
CPC .................... C07K 14/7155; A61K 38/1793
See application file for complete search history.

(56) References Cited

U.S. PATENT DOCUMENTS

| | | |
|---|---|---|
| 11,267,866 B2 | 3/2022 | Soon-Shiong |
| 2009/0226435 A1 | 9/2009 | Khare |
| 2012/0177595 A1 | 7/2012 | Wong et al. |
| 2014/0255341 A1 | 9/2014 | Kalinski et al. |
| 2014/0294835 A1 | 10/2014 | Moore et al. |
| 2017/0020963 A1 | 1/2017 | Qu et al. |
| 2017/0087185 A1 | 3/2017 | Crane et al. |
| 2017/0342119 A1 | 11/2017 | Liu et al. |

FOREIGN PATENT DOCUMENTS

| | | |
|---|---|---|
| EP | 2 724 727 A1 | 4/2014 |
| WO | 2012/040323 A2 | 3/2012 |
| WO | 2017/222619 A2 | 12/2017 |
| WO | 2019/195420 A1 | 10/2019 |

OTHER PUBLICATIONS

Shurin et al., "Loss of New Chemokine CXCL 14 in Tumor Tissue Is Associated with Low Infiltration by Dendritic Cells (DC), while Restoration of Human CXCL 14 Expression in Tumor Cells Causes Attraction of DC Both In Vitro and In Vivo", J Immunol, vol. 174, No. 9, May 1, 2005, pp. 5490-5498.
Ghasemzadeh et al., "New Strategies in Bladder Cancer: A Second Coming for Immunotherapy", Clin Cancer Res, vol. 22, No. 4, Feb. 15, 2016, pp. 793-801.
International Search Report and Written Opinion received for PCT Application Serial No. PCT/US2019/025581 dated Jul. 16, 2019, 14 pages.
Cicchini et al., "Suppression of Antitumor Immune Responses by Human Papillomavirus through Epigenetic Downregulation of CXCL 14", American Society for Microbiology May/Jun. 2016, vol. 7, Issue 3, pp. 1-13.
Linch et al., "OX40 agonists and combination immunotherapy: putting the pedal to the metal", Frontiers in Oncology, vol. 5, Article 34, Feb. 2015, pp. 1-14.
Kostianovsky et al., "Astrocytic Regulation of Human Monocytic/Microglial Activation", The Journal of Immunology, vol. 181, No. 8, Oct. 15, 2008, pp. 5425-5432.
Razavi et al., "Immune Evasion Strategies of Glioblastoma", Frontiers in Surgery, vol. 3, No. 11, Mar. 2, 2016, pp. 1-9.
International Preliminary Report on Patentability Chapter I received for PCT Application Serial No. PCT/US2019/025581 dated Oct. 15, 2020, 10 pages.
Beavis et al., "Reprogramming the tumor microenvironment to enhance adoptive cellular therapy", Seminars in Immunology, vol. 28, No. 1, Feb. 2016, pp. 1-9.
Notice of Allowance received for U.S. Appl. No. 17/041,377 dated Nov. 2, 2021, 27 pages.

*Primary Examiner* — Prema M Mertz
(74) *Attorney, Agent, or Firm* — Martin Fessenmaier; Umberg Zipser LLP

(57) ABSTRACT

Compositions, methods, and uses of recombinant immunoglobulin proteins, recombinant immunoglobulin protein complexes, carrier protein complexes, and a pharmaceutical composition including one or more of those to increase immune therapy effectiveness are presented. Preferred protein and protein complex comprise one or more functional moieties that includes a binding motif to a tumor-associated antigen, a T-cell activating molecule, and a chemokine. In some embodiments, the pharmaceutical composition includes two or more protein complexes, which are functionally distinct from each other. In other embodiments, the pharmaceutical composition includes a genetically-engineered microorganism including a first tumor-associated antigen and a T-cell activating molecule, a recombinant immunoglobulin protein complex, and a chemokine.

17 Claims, No Drawings

ADVANCED AVATAR DENDRITIC CELLS

This application is a continuation application of our copending allowed U.S. patent application with the Ser. No. 17/041,377, which was filed Sep. 24, 2020, which is a 371 application of International application with the Ser. No. PCT/US2019/025581, which was filed Apr. 3, 2019, and which claims priority to U.S. Provisional application with the Ser. No. 62/652,554, filed Apr. 4, 2018, all of which are incorporated in their entirety herein.

FIELD OF THE INVENTION

The field of the invention is immunotherapy, especially as it relates to cancer immune therapy with multiple treatment modalities.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Single small-molecule drug cancer treatments generally fail to provide a cure, due to among other things, the high complexity of tumor biology. For the same reason, multi-drug treatment regimens tend to fail in removing all cancer cells from a patient, and relapse is often simply a question of time. For example, it has become apparent that many tumor cells create a complex tumor microenvironment (TME) that typically includes regulatory T cells (Tregs), myeloid derived suppressor cells (MDSCs), and tumor associated macrophages (TAMs) that prevent immune surveillance by endogenous T cells and natural killer (NK) cells, reduce antigen presentation, and hinder the activity of adoptively transferred anti-tumor T cells (*Front Surg* 2016; 3:11; *J Immunol* 2008; 181:5425-5432; or *Semin Immunol* 2016; 28:64-72).

Consequently, various attempts have been undertaken to modulate the tumor microenvironment to thereby enhance treatment effects. For example, US 2017/0087185 discloses the use of a lentiviral expression system for the generation of genetically engineered monocytes and monocyte-derived macrophages for immunotherapy. In US 2017/0231995, Bruton's tyrosine kinase (BTK) inhibitors are discussed to interfere with signaling between tumor cells and various immune competent cells within the tumor microenvironment. In yet another approach, as discussed in US 2014/0255341, therapeutic agents are used that increase local production of effector cell-attracting chemokines within a tumor, with concomitant suppression of local production of chemokines that attract regulatory T(reg) cells. For example, such therapeutic agents include Toll-like receptor (TLR) agonists or other activators of NF-KB pathway in combination with a blocker of prostaglandin synthesis or a blocker of prostaglandin signaling, in combination with a type-1 interferon, or in combination with both a blocker of prostaglandin synthesis or signaling and with a type-1 interferon.

In addition, more attention has been grown to the use of chemokines that attracts immune competent cell to the tumor microenvironment. For example, loss of chemokine CXCL14 was reported to be associated with low infiltration by dendritic cells, and overexpression of CXCL14 could attract dendritic cell toward the tumor in vitro and in vivo (*J Immunol* 2005; 174:5490-5498). Further, expression of CXCL14 by tumor cells could also increases natural killer (NK), CD4+ T, and CD8+ T cell infiltration, implicating CXCL14 as a candidate of immune modulatory reagents in the treatment regime for the cancer patient.

While those individual candidate treatment method, target and reagents may improve selected aspects of treatment, they still often fail to lead to complete remission of the tumor. Moreover, most of the known treatments may also have systemic effects due to the lack of specificity of action in the tumor microenvironment. Viewed from a different perspective, all or almost all of the known treatments target only a single aspect of tumor biology. Therefore, there remains a need for improved compositions and methods to treat cancer using immune therapy.

SUMMARY OF THE INVENTION

The inventive subject matter is directed to various compositions of, methods for, and use of a recombinant protein or protein complex or pharmaceutical compositions including a recombinant protein or protein complexes to increase effectiveness of immune therapy in the cancer patients. The recombinant protein or protein complex or pharmaceutical compositions includes a plurality of functional moieties that may affect the tumor microenvironment from different aspects. Thus, one aspect of the inventive subject matter includes a recombinant immunoglobulin protein complex that includes an Fc domain having two Fc portions, each of which is coupled with a cytokine binding domain having a functional moiety. Each cytokine binding domain is coupled with a cytokine, and each of the cytokine is coupled with a functional moiety. It is especially preferred that at least two of the first, second, third, and fourth functional moieties are functionally distinct, and the first, second, third, and fourth functional moieties are selected from a group consisting of a binding motif to a tumor-associated antigen, a T-cell activating molecule, and a chemokine.

Optionally, in this recombinant immunoglobulin protein complex, at least one of the first and second cytokine binding domains is IL-15Rα, or modified IL-15Rα that decreases interaction with IL-15Rβ or IL-15Rγ and cytokines binding to such cytokine binding domain is IL-15 or mutated IL-15 such that the cytokine binding domain and cytokine of the recombinant immunoglobulin protein complex present strong IL-15 agonist function.

Also optionally, the binding motif to a tumor-associated antigen is an antibody, a portion of an antibody or single-chain variable fragment (scFv) that is specific to any tumor-associated antigen, preferably EGFR or its fragment thereof, or more preferably patient-specific tumor-specific neoepitope. With respect to T-cell activating molecule, T-cell activating molecule can be selected from a group consisting of an OX-40 ligand, a 4-1BB ligand, an OX-40 agonist antibody, a 4-1BB agonist antibody. A preferred chemokine may include CXCL-14.

In some embodiments, the recombinant immunoglobulin protein complex may further include a fifth functional moiety that is coupled to N-terminus of at least one of the first and second Fc portions via a linker or that is coupled at least one of the first cytokine binding domain or the first cytokine via a linker. In such embodiments, it is preferred that the linker is an acid-labile linker that can be cleaved in an acidic tumor microenvironment. Alternatively and/or additionally, the recombinant immunoglobulin protein complex may further include a fifth functional moiety that is coupled to at least one of the first cytokine binding domain or the first cytokine via a linker. In such embodiments, it is contemplated that the fifth functional moiety and the first functional moiety are coupled to the first cytokine binding domain, wherein the linker comprises first and second sublinkers, and wherein the first sublinker is coupled to the first functional moiety and the second sublinker is coupled to the fifth functional moiety.

The contemplated recombinant immunoglobulin protein complex may further be coupled to a carrier protein via the Fc domain. Preferred carrier protein can be selected from the following: protein A, protein G, protein Z, albumin, refolded albumin. Additionally, the carrier protein can be further associated with an immune-stimulatory cytokine or a chemokine that are coupled to the carrier protein via a linker.

In another aspect of the inventive subject matter, the inventors contemplate a pharmaceutical composition that includes a plurality of recombinant immunoglobulin protein complexes. Each of the recombinant immunoglobulin protein complexes includes an Fc domain having two Fc portions, each of which is coupled with a cytokine binding domain having a functional moiety. Each cytokine binding domain is coupled with a cytokine, and each of the cytokine is coupled with a functional moiety. It is especially preferred that at least two of the first, second, third, and fourth functional moieties are functionally distinct, and the first, second, third, and fourth functional moieties are selected from a group consisting of a binding motif to a tumor-associated antigen, a T-cell activating molecule, and a chemokine. Preferably, the pharmaceutical composition includes at least three recombinant immunoglobulin protein complexes, and the at least three recombinant immunoglobulin protein complexes are functionally distinct from each other.

Optionally, in this recombinant immunoglobulin protein complex, at least one of the first and second cytokine binding domains is IL-15Rα, or modified IL-15Rα that decreases interaction with IL-15Rβ or IL-15Rγ and cytokines binding to such cytokine binding domain is IL-15 or mutated IL-15 such that the cytokine binding domain and cytokine of the recombinant immunoglobulin protein complex present strong IL-15 agonist function.

Also optionally, the binding motif to a tumor-associated antigen is an antibody, a portion of an antibody or single-chain variable fragment (scFv) that is specific to any tumor-associated antigen, preferably EGFR or its fragment thereof, or more preferably patient-specific tumor-specific neoepitope. With respect to T-cell activating molecule, T-cell activating molecule can be selected from a group consisting of an OX-40 ligand, a 4-1BB ligand, an OX-40 agonist antibody, a 4-1BB agonist antibody. A preferred chemokine may include CXCL-14.

In some embodiments, the recombinant immunoglobulin protein complex may further include a fifth functional moiety that is coupled to N-terminus of at least one of the first and second Fc portions via a linker or that is coupled at least one of the first cytokine binding domain or the first cytokine via a linker. In such embodiments, it is preferred that the linker is an acid-labile linker that can be cleaved in an acidic tumor microenvironment. Alternatively and/or additionally, the recombinant immunoglobulin protein complex may further include a fifth functional moiety that is coupled to at least one of the first cytokine binding domain or the first cytokine via a linker. In such embodiments, it is contemplated that the fifth functional moiety and the first functional moiety are coupled to the first cytokine binding domain, wherein the linker comprises first and second sublinkers, and wherein the first sublinker is coupled to the first functional moiety and the second sublinker is coupled to the fifth functional moiety.

The contemplated recombinant immunoglobulin protein complex may further be coupled to a carrier protein via the Fc domain. Preferred carrier protein can be selected from the following: protein A, protein G, protein Z, albumin, refolded albumin. Additionally, the carrier protein can be further associated with an immune-stimulatory cytokine or a chemokine that are coupled to the carrier protein via a linker.

Optionally, the pharmaceutical composition may further include a reagent upregulating CXCL-14 expression in a tumor cell, which may include histone deacetylase (HDAC) inhibitor.

In still another aspect of the inventive subject matter, the inventors contemplate a pharmaceutical composition that includes 1) a genetically-engineered microorganism that has a recombinant nucleic acid encoding a first tumor-associated antigen and a T-cell activating molecule, 2) a recombinant immunoglobulin protein complex, and 3) a chemokine. The recombinant immunoglobulin protein complex includes an Fc domain having two Fc portions, each of which is coupled with a cytokine binding domain having a functional moiety, and cytokines that are coupled to the cytokine binding domain. It is contemplated that at least one of the first and second functional moieties is a binding motif to a second tumor-associated antigen.

Optionally, the genetically-engineered microorganism is selected from a group consisting of a virus, an yeast, a bacteria. Also optionally, the recombinant nucleic acid encodes a polytope. Also optionally, the first tumor-associated antigen is a patient-specific and tumor specific neoepitope.

With respect to T-cell activating molecule, T-cell activating molecule can be selected from a group consisting of an OX-40 ligand, a 4-1BB ligand, an OX-40 agonist antibody, a 4-1BB agonist antibody. A preferred chemokine may include CXCL-14. Optionally, in this recombinant immunoglobulin protein complex, at least one of the first and second cytokine binding domains is IL-15Rα, or modified IL-15Rα that decreases interaction with IL-15Rβ or IL-15Rγ and cytokines binding to such cytokine binding domain is IL-15 or mutated IL-15 such that the cytokine binding domain and cytokine of the recombinant immunoglobulin protein complex present strong IL-15 agonist function.

In some embodiments, the first and second tumor-associated antigens are same peptide antigens. Optionally, the second tumor-associated antigen is a patient-specific and tumor specific neoepitope and/or a portion of EGFR.

Additionally and/or alternatively, the chemokine is CXCL-14, and/or the chemokine is coupled to the recombinant immunoglobulin protein complex via a linker, preferably an acid-labile linker. In such embodiments, it is contemplated that the chemokine can be the at least one of the first and second functional moieties and/or the chemokine is coupled to the recombinant immunoglobulin protein complex N-terminus of at least one of the first and second Fc portions.

Another aspect of the inventive subject matter includes a method of enhancing immunotherapy or increasing effectiveness of immune therapy in a patient having a tumor. In this method, a recombinant immunoglobulin protein including an Fc domain having two Fc portions, each of which is coupled with a cytokine binding domain having a functional moiety is provided. Each cytokine binding domain is coupled with a cytokine, and each of the cytokine is coupled with a functional moiety. It is especially preferred that at least two of the first, second, third, and fourth functional moieties are functionally distinct, and the first, second, third, and fourth functional moieties are selected from a group consisting of a binding motif to a tumor-associated antigen, a T-cell activating molecule, and a chemokine. Then, the recombinant immunoglobulin protein is administered to the patient in a dose and schedule effective to treat the tumor.

Optionally, in this recombinant immunoglobulin protein complex, at least one of the first and second cytokine binding domains is IL-15Rα, or modified IL-15Rα that decreases interaction with IL-15Rβ or IL-15Rγ and cytokines binding to such cytokine binding domain is IL-15 or mutated IL-15 such that the cytokine binding domain and cytokine of the recombinant immunoglobulin protein complex present strong IL-15 agonist function.

Also optionally, the binding motif to a tumor-associated antigen is an antibody, a portion of an antibody or single-chain variable fragment (scFv) that is specific to any tumor-associated antigen, preferably EGFR or its fragment thereof, or more preferably patient-specific tumor-specific neoepitope. With respect to T-cell activating molecule, T-cell activating molecule can be selected from a group consisting of an OX-40 ligand, a 4-1BB ligand, an OX-40 agonist antibody, a 4-1BB agonist antibody. A preferred chemokine may include CXCL-14.

In some embodiments, the recombinant immunoglobulin protein complex may further include a fifth functional moiety that is coupled to N-terminus of at least one of the first and second Fc portions via a linker or that is coupled at least one of the first cytokine binding domain or the first cytokine via a linker. In such embodiments, it is preferred that the linker is an acid-labile linker that can be cleaved in an acidic tumor microenvironment. Alternatively and/or additionally, the recombinant immunoglobulin protein complex may further include a fifth functional moiety that is coupled to at least one of the first cytokine binding domain or the first cytokine via a linker. In such embodiments, it is contemplated that the fifth functional moiety and the first functional moiety are coupled to the first cytokine binding domain, wherein the linker comprises first and second sublinkers, and wherein the first sublinker is coupled to the first functional moiety and the second sublinker is coupled to the fifth functional moiety.

The contemplated recombinant immunoglobulin protein complex may further be coupled to a carrier protein via the Fc domain. Preferred carrier protein can be selected from the following: protein A, protein G, protein Z, albumin, refolded albumin. Additionally, the carrier protein can be further associated with an immune-stimulatory cytokine or a chemokine that are coupled to the carrier protein via a linker.

Still another aspect of the inventive subject matter includes a method of enhancing immunotherapy or increasing effectiveness of immune therapy in a patient having a tumor. In this method, a pharmaceutical composition including a plurality of recombinant immunoglobulin protein complexes is provided. Each of the recombinant immunoglobulin protein complexes includes 1) an Fc domain having first and second Fc portions coupled with respective first and second cytokine binding domains having respective first and second functional moieties, 2) a first and second cytokines coupled with a third and fourth functional moieties, where the first and second cytokine binding domains are coupled to. In this composition, at least two of the first, second, third, and fourth functional moieties are functionally distinct, and the first, second, third, and fourth functional moieties are selected from a group consisting of a binding motif to a tumor-associated antigen, a T-cell activating molecule, and a chemokine. Preferably, at least two of the recombinant immunoglobulin protein complexes functionally distinct. Then, the pharmaceutical composition is administered to the patient in a dose and schedule effective to treat the tumor.

Optionally, the genetically-engineered microorganism is selected from a group consisting of a virus, an yeast, a bacteria. Also optionally, the recombinant nucleic acid encodes a polytope. Also optionally, the first tumor-associated antigen is a patient-specific and tumor specific neoepitope.

With respect to T-cell activating molecule, T-cell activating molecule can be selected from a group consisting of an OX-40 ligand, a 4-1BB ligand, an OX-40 agonist antibody, a 4-1BB agonist antibody. A preferred chemokine may include CXCL-14. Optionally, in this recombinant immunoglobulin protein complex, at least one of the first and second cytokine binding domains is IL-15Rα, or modified IL-15Rα that decreases interaction with IL-15Rβ or IL-15Rγ and cytokines binding to such cytokine binding domain is IL-15 or mutated IL-15 such that the cytokine binding domain and cytokine of the recombinant immunoglobulin protein complex present strong IL-15 agonist function.

In some embodiments, the first and second tumor-associated antigens are same peptide antigens. Optionally, the second tumor-associated antigen is a patient-specific and tumor specific neoepitope and/or a portion of EGFR.

Additionally and/or alternatively, the chemokine is CXCL-14, and/or the chemokine is coupled to the recombinant immunoglobulin protein complex via a linker, preferably an acid-labile linker. In such embodiments, it is contemplated that the chemokine can be the at least one of the first and second functional moieties and/or the chemokine is coupled to the recombinant immunoglobulin protein complex N-terminus of at least one of the first and second Fc portions.

Still another aspect of the inventive subject matter includes a method of enhancing immunotherapy or increasing effectiveness of immune therapy in a patient having a tumor. In this method, a pharmaceutical composition including at least two of 1) a genetically-engineered microorganism that has a recombinant nucleic acid encoding a first tumor-associated antigen and a T-cell activating molecule, 2) a recombinant immunoglobulin protein complex, and 3) a chemokine. The recombinant immunoglobulin protein complex includes an Fc domain having two Fc portions, each of which is coupled with a cytokine binding domain having a functional moiety, and cytokines that are coupled to the cytokine binding domain. It is contemplated that at least one of the first and second functional moieties is a binding motif to a second tumor-associated antigen. Then, the pharmaceutical composition is administered to the patient in a dose and schedule effective to treat the tumor.

Optionally, the genetically-engineered microorganism is selected from a group consisting of a virus, an yeast, a bacteria. Also optionally, the recombinant nucleic acid encodes a polytope. Also optionally, the first tumor-associated antigen is a patient-specific and tumor specific neoepitope.

With respect to T-cell activating molecule, T-cell activating molecule can be selected from a group consisting of an OX-40 ligand, a 4-1BB ligand, an OX-40 agonist antibody, a 4-1BB agonist antibody. A preferred chemokine may include CXCL-14. Optionally, in this recombinant immunoglobulin protein complex, at least one of the first and second cytokine binding domains is IL-15R$\alpha$, or modified IL-15R$\alpha$ that decreases interaction with IL-15R$\beta$ or IL-15R$\gamma$ and cytokines binding to such cytokine binding domain is IL-15 or mutated IL-15 such that the cytokine binding domain and cytokine of the recombinant immunoglobulin protein complex present strong IL-15 agonist function.

In some embodiments, the first and second tumor-associated antigens are same peptide antigens. Optionally, the second tumor-associated antigen is a patient-specific and tumor specific neoepitope and/or a portion of EGFR.

Additionally and/or alternatively, the chemokine is CXCL-14, and/or the chemokine is coupled to the recombinant immunoglobulin protein complex via a linker, preferably an acid-labile linker. In such embodiments, it is contemplated that the chemokine can be the at least one of the first and second functional moieties and/or the chemokine is coupled to the recombinant immunoglobulin protein complex N-terminus of at least one of the first and second Fc portions.

In still another aspect of the inventive subject matter, the inventors contemplate use of the pharmaceutical compositions or the recombinant immunoglobulin protein complex described above for enhancing immunotherapy or increasing effectiveness of immune therapy in a patient having a tumor.

Various objects, features, aspects and advantages of the inventive subject matter will become more apparent from the following detailed description of preferred embodiments.

DETAILED DESCRIPTION

The inventors now discovered that the effectiveness of immune therapy, and particularly NK-cell or T-cell based immune therapy to a cancer patient can be enhanced by specifically delivering a plurality of anti-cancer drugs to the tumor microenvironment to so recruit NK or T cells to the tumor microenvironment and/or induce tumor-specific NK or T cell-mediated immune response.

Along the line, the inventors discovered that a recombinant protein complex or a pharmaceutical composition including a recombinant protein complex that has a plurality of functional moieties can be generated to treat the tumor. At least some functional moieties can be drug molecules. As used herein, a drug molecule can be any molecule that can treat a tumor to reduce the tumor growth, tumor cell activity, metastasis of the tumor, reduce immune suppression in the tumor microenvironment, boost the effect of other cancer treatments, or that can monitor the progress or effect of other cancer treatment including immune therapy. For example, the drug molecule may be an anti-cancer drug such that providing the anti-cancer drug in the tumor microenvironment could boost effectiveness of the immune therapy in a location-specific manner. In another example, the drug molecule may be a marker molecule such that the activity of the cytotoxic immune cells in the tumor microenvironment can be determined by administering a modified immune competent cell coupled with the marker molecule.

Thus, in an especially preferred aspect of the inventive subject matter, the inventors contemplate a recombinant immunoglobulin protein complex having a plurality of functional moieties, among which at least one of the functional moiety is configured to target the recombinant immunoglobulin protein complex to the tumor microenvironment, and at least another functional moiety is configured to induce T cell or NK cell mediated immune response in the tumor microenvironment. Such multi-functional recombinant protein is thought to increase the effectiveness of the functional moieties, especially those induces immune response, by specifically directing them to the tumor microenvironment, and even targeting them to a specific cell types in the tumor microenvironment. As is discussed in more detail below, the multi-functional recombinant protein, in some aspects of the inventive subject matter, may be based on a TxM scaffold or modified IL-15 superagonist (ALT-803) (e.g., as shown in http://www.altorbioscience.com/our-science/il-15-protein-superagonist-and-scaffold-technology/)

As used herein, the term "tumor" refers to, and is interchangeably used with one or more cancer cells, cancer tissues, malignant tumor cells, or malignant tumor tissue, that can be placed or found in one or more anatomical locations in a human body. As used herein, the term "bind" refers to, and can be interchangeably used with a term "recognize" and/or "detect", an interaction between two molecules with a high affinity with a $K_D$ of equal or less than $10^{-3}$ M, $10^{-4}$ M, $10^{-5}$ M, $10^{-6}$ M, or equal or less than $10^{-7}$ M. As used herein, the term "provide" or "providing" refers to and includes any acts of manufacturing, generating, placing, enabling to use, or making ready to use.

In one exemplary and especially preferred aspect of the inventive subject matter, the inventors contemplate a recombinant immunoglobulin protein complex having a plurality of functional moieties. Most typically, the recombinant immunoglobulin protein complex comprises or mimics an ALT-803 or TxM structure. Of course, it is also contemplated that the recombinant immunoglobulin protein complex may also mimic a phenotype of human immunoglobulin A or M such that multiple recombinant immunoglobulin protein complexes form a larger, multiple-unit, complex.

While it is preferred that the Fc portion is substantially a full size Fc domain of a human IgG, IgM, IgE, or IgA for fully functional Fc dependent reaction (e.g., antibody-dependent cellular cytotoxicity (ADCC), etc.), it is also contemplated that Fc portion can be a fragment of the full size Fc domain of human IgG, IgM, IgE, or IgA. Yet, it is especially preferred that the Fc portion will include sufficient sequence to allow (i) formation of dimers via a disulfide bond, (ii) binding to protein A or protein G, and/or (iii) binding to the Sudlow-II domain of albumin, and especially refolded albumin (which may be loaded with a drug such as a taxane). For example, each of the two Fc portions includes a hydrophobic interface to interact with each other to form a dimer. The hydrophobic interface includes at least 10 amino acids, at least 15 amino acids, at least 20 amino acids, at least 25 amino acids, similar to Fc domain of human immunoglobulin G. Alternatively, at least one of the two Fc portions can be engineered such that the single Fc portion can be stable and soluble without forming a dimer with another Fc portion.

Each of the Fc portion is typically coupled with a cytokine binding domain at the N-terminus of the Fc portion, and each of the cytokine binding domain is bound to a ligand (a cytokine molecule). Any suitable cytokine binding domains are contemplated, including, but not limited to interleukin- 15 (IL-15) binding protein (e.g., a full length or an IL-15 binding motif of IL-15 receptor α, etc.), CD25 (IL-2 binding protein), IL-4 receptor α, IL-13 receptor α, or IL-21 receptor α. Of course, the preferred cytokine is the high affinity ligand for the cytokine binding domains, for example, IL-15 for a full length or an IL-15 binding motif of IL-15 receptor α, and IL-2 for CD25. In some embodiments, the cytokine binding domain is directly coupled to the N-terminus of Fc portion. In other embodiments, the cytokine binding domain is coupled to the N-terminus of Fc portion via a linker or a spacer, which is typically between 3-30 amino acids, preferably between 5-20 amino acids, more preferably between 5-15 amino acids. The inventors contemplate that glycine-rich sequences (e.g., gly-gly-ser-gly-gly, etc.) are preferred to provide structural flexibility between the Fc portion and the cytokine binding domain, especially when the cytokine binding domain is bulky and may provide steric hindrance to other nearby domains. The inventors also contemplate that in some embodiments, at least one of the cytokine binding domains and cytokines coupled to those can be substituted with other pairs of molecules coupled by high affinity protein-protein interaction. For example, the pairs of molecules may include an enzyme (preferably inactive enzyme)-peptide substrate, or a toxin receptor-inactive toxin (e.g., recombinant fusion toxin).

In some embodiments, the cytokine binding domain can be modified to reduce the biological effect of cytokine binding to the binding domain. For example, where the cytokine binding domain is IL-15 receptor α (IL-15Rα), and the cytokine is IL-15, the IL-15Rα:IL-15 complex can trans-interact with a membrane-bound IL-15 receptor β and IL-15 receptor γ to elicit IL-15-mediated signaling cascade in the cell expressing IL-15 receptor β and IL-15 receptor γ. Thus, the inventors contemplate that a portion of the IL-15Rα can be modified so that the interaction between the IL-15Rα:IL-15 and IL-15 receptor β or IL-15 receptor γ can be prevented. For example, a portion of IL-15Rα critical for interaction with IL-15 receptor β or IL-15 receptor γ may be removed or mutated such that the interaction can be abolished. In another example, an extra peptide motif can be added to the IL-15Rα such that the recognition of IL-15 receptor β or IL-15 receptor γ of IL-15Rα-IL-15 may be interfered.

Alternatively and/or additionally, the cytokine can be modified to reduce such undesired effect. For example, where the cytokine is IL-15, IL-15 peptide can be modified to reduce the affinity to IL-15 receptor β or IL-15 receptor γ (e.g., deletion or substitution of amino acids of IL-15 at positions 8, 61, 65. 72, 92, 101, 108, or 111 etc.). Other exemplary mutations that may reduce the affinity of IL-15 to IL-15 receptor β or IL-15 receptor y are disclosed in U.S. Patent Pub. No. US2012/0177595, which is incorporated herein by reference in its entirety.

The inventors contemplate that one or more cytokine binding domains and cytokines in the recombinant immunoglobulin protein complex, more preferably each of the cytokine binding domains and cytokines, are coupled with one or more functional moieties. While any desired functional moieties are contemplated, in an especially preferred embodiment, at least one functional moiety is a binding motif to a tumor-associated antigen, preferably a patient-specific and/or tumor-specific neoepitope. As used herein, the tumor-associated antigen refers any antigen that can be presented on the surface of the tumor cells, which includes an inflammation-associated peptide antigen, a tumor associated peptide antigen, a tumor specific peptide antigen, and a cancer neoepitope. Thus, a tumor-associated antigen can include any peptide antigens and/or mutant peptide antigens that are specifically expressed on the tumor cells or overexpressed on the tumor cells. For example, the tumor-associated antigen may include a portion of epidermal growth factor receptor (EGFR), preferably, human epidermal growth factor receptor 2 (HER2), CEA, MUC-1, CYPB1, PSA, brachyury, PD-L1, etc. Typically, the tumor associated antigens and neoepitopes (which are typically patient-specific and tumor-specific) can be identified from the omics data obtained from the cancer tissue of the patient or normal tissue (of the patient or a healthy individual), respectively. Omics data typically includes information related to genomics, transcriptomics, and proteomics. As used herein, the cancer cells or normal cells (or tissues) may include cells from a single or multiple different tissues or anatomical regions, cells from a single or multiple different hosts, as well as any permutation of combinations.

Any suitable binding motif (affinity portion) that can be linked to the cytokine binding domain (e.g., IL-15Rα of TxM) or cytokine (e.g., IL-15 of TxM) of the recombinant immunoglobulin protein complex without providing significant steric hindrance or functional defect and that binds specifically to tumor associated antigens and/or neoepitopes are contemplated. Preferred binding motif includes a whole antibody (e.g., IgG, IgM, IgE, and/or IgA), a portion of an antibody (e.g., one or more Fab, Fab', F(ab)$_2$, etc.), or a single chain variable fragment (scFv). Alternatively, suitable affinity portions may also include proteins that were obtained by affinity maturation (e.g., using phage display) or by RNA display. In some embodiments, the protein complex may include one or more binding motifs that target same tumor-associated antigen (e.g., two scFv binding to Her-2, coupled to two cytokine binding domains, respectively). Alternatively and/or additionally, the protein complex may include one or more binding motifs that target different tumor-associated antigens (e.g., one scFv binding to Her2 that is coupled to one cytokine binding domain and another scFv binding to a patient-specific tumor specific neoepitope that is coupled to another cytokine binding domain, etc.). Alternatively and/or additionally, the protein complex may include have mixed combination of one or more binding motifs that target same tumor-associated antigen and one or more binding motifs that target different tumor-associated antigens. For example, the protein complex may include first scFv binding to Her2 that is coupled to one cytokine binding domain and second and third scFvs binding to PD-L1 and a patient-specific tumor specific neoepitope respectively that are coupled to another cytokine binding domain. In such embodiments, it is contemplated that the second and third scFvs are coupled via a linker.

The inventors further contemplate that the recombinant immunoglobulin protein complex also include an immune effector molecule, preferably a molecule that can induce T cell activation, that are coupled to at least one of cytokine binding domain or cytokine of the protein complex. Any suitable peptide, peptide fragment, and/or synthetic peptide that can increase T cell activation at least 5%, at least 10%, at least 20%, at least 30% are contemplated. Exemplary T cell activating molecule includes, but not limited to, an OX-40 ligand, a 4-1BB ligand, an OX-40 agonist antibody, a 4-1BB agonist antibody. It is contemplated that binding of these exemplary T cell activating molecule to T cell may mimic the dendritic cell-T cell interaction to induce T cell activation.

Such contemplated protein complex that includes IL-15, tumor-associate antigen binding motif and T cell activating molecule are expected to provide several notable advantages. Where the protein complex has an scFv that binds tumor associated antigen, the protein complex is specifically targeted towards tumor cells in the tumor microenvironment. In addition, the presence of the IL-15 or IL-15 superagonist will advantageously attract and activate T cells and NK cells, while the presence of the Fc portion facilitates ADCC. Further, co-presence of T cell activating molecule (e.g., OX-40 agonist antibody, a 4-1BB agonist antibody, etc.) can further augment T cell activation in the tumor microenvironment where the T cells are more likely to interact with antigen presenting cells or tumor cells that present tumor-associated antigens or neoepitopes such that more T cells can be activated in an tumor-antigen specific manner.

In a further preferred embodiment, the inventors contemplate that the recombinant immunoglobulin protein complex also includes an immune stimulatory cytokine (e.g., IL-2, IL-8, etc.) and a chemokine (e.g., CXCL14, CD40L, CCL2, CCL1, CCL22, CCL17, CXCR3, CXCL9, CXCL10, CXCL11, CXCL14, etc.), which can attract immune competent cells (e.g., T cells, B cells, NK cells, NKT cells, dendritic cells, macrophage etc.) to the tumor microenvironment and/or activate the immune competent cells.

In some embodiments, the cytokine binding domain or cytokine is directly coupled to a functional moiety (e.g., via a cross-linker that uses thiol or amino groups, non-covalent coupling using hydrogen bonding or hydrophobic interactions, etc.). Alternatively and/or additionally, the cytokine binding domain or cytokine is coupled to a functional moiety via a linker or a spacer, which is typically between 3-30 amino acids, preferably between 5-20 amino acids, more preferably between 5-15 amino acids. Similar to coupling between the Fc portion and the cytokine binding domain, glycine-rich sequences (e.g., gly-gly-ser-gly-gly, etc.) as a linker or a spacer are preferred to provide structural flexibility between the cytokine binding domain (or cytokine) and the target recognition domain, especially when one or more target recognition domain is bulky and may provide steric hindrance to other target recognition domains.

Optionally, especially where the functional moiety is preferred to be released in the tumor microenvironment rather than being tethered to the protein complex, the functional moiety can be coupled to one of the cytokine binding domain or cytokine via a linker that can be preferably cleaved in the tumor microenvironment. While any suitable linkers that can be preferentially cleaved in the tumor microenvironment and/or upon activation of immune system are contemplated, one preferred linker includes a linker that is cleavable in a mild acidic environment (e.g., at a pH between 3-6, at a pH between 4-6, at a pH between 4.5-5.5, etc.), yet stable in a neutral pH. For example, preferred acid-labile linkers include a thimaleamic acid linker and an acid-cleavable hydrazine linker (e.g., hydrazine linker, etc.). It is contemplated that any functional moieties including a drug molecule (either an anti-cancer drug or a marker molecule) coupled to the immune competent cell via an acid-labile linker can be released in the mildly acidic tumor microenvironment, such that the functional moieties can selectively and specifically target the tumor microenvironment.

In some embodiments, a linker may comprise a plurality of sublinkers that are connected to one support (e.g., similar to a dendrimer structure), where the support is coupled to the immune competent cells. For the plurality of sublinkers, it is contemplated that at least two sublinkers have different linker types such that the linkers can be cleaved or cannot be cleaved in different conditions. For example, the linker may include an acid-labile linker that is conjugated with a chemokine (e.g., CXCL14) and a glycine-rich linker that is conjugated with T cell activating molecule (e.g., OX-40 ligand). In such example, the chemokine can be cleaved and released when the immune competent cell enters the acidic tumor microenvironment, but the T cell activating molecule may stay conjugated in the protein complex in the same condition. However, it is also contemplated that the at least two sublinkers are same type of linkers such that linkers can be cleaved in the same condition.

While it is preferred that the functional moieties are coupled to either cytokine binding domain or cytokine of the recombinant immunoglobulin protein complex, it is also contemplated that one or more functional moieties can be coupled to Fc domain of the recombinant immunoglobulin protein complex. In such embodiment, it is especially preferred that the functional moieties are coupled to the Fc domain via a cleavable linker such that ADCC mediated by Fc domain may not be prevented by functional moieties. Thus, one exemplary recombinant immunoglobulin protein complex may be based on TxM that includes dimerized Fc domain, two IL-15 binding domain and two IL-15. Each of IL-15 binding domains is coupled with an scFv binding to HER-2 fragment via a glycine-rich linker, and each of IL-15 is coupled to an OX-40 ligand and a 4-1BB ligand via a dendrimer-type linker that includes two glycine-rich sublinkers that are coupled to OX-40 ligand or a 4-1BB ligand, respectively. In each of N-terminus of Fc portions of Fc domain, CXCL14 is coupled to the Fc portion via an acid-labile linker.

Additionally, the recombinant immunoglobulin protein complex can be further coupled to a carrier molecule via Fc portion. Any pharmaceutically acceptable carrier molecules that can stably carry the recombinant immunoglobulin protein complex to the tumor microenvironment are contemplated. Exemplary carrier molecules includes protein A, protein G, protein Z, albumin, refolded albumin, a nanoparticle (e.g., quantum dots, gold nanoparticles, magnetic nanoparticles, nanotubes, polymeric nanoparticles, dendrimers, etc.), or a bead (e.g., polystyrene bead, latex bead, dynabead, etc.). Preferably, the nanoparticle and/or beads have a dimension below 1 µm, preferably below 100 nm.

Alternatively and additionally, it is also contemplated that one or more immune-stimulatory cytokine or chemokine can be coupled to the carrier protein via a linker such that the carrier molecule carries two distinct molecules: 1) a recombinant immunoglobulin protein complex and 2) a cytokine or a chemokine. In such embodiments, the immune-stimulatory cytokine or chemokine can be coupled to an anchor molecule that can be anchored to the carrier molecule directly or indirectly. For example, where the carrier protein is an albumin, the anchor molecule can be a hydrophobic peptide or glycolipids in any suitable size (e.g., in a length of at least 10 amino acids, 15 amino acids, 20 amino acids, 30 amino acids, etc.) to fit in one of Sudlow's site I and II of the albumin or any other hydrophobic area of the albumin.

In other aspect of the inventive subject matter, the inventors contemplate a pharmaceutical composition that includes a plurality of distinct recombinant immunoglobulin protein complexes. As used herein, recombinant immunoglobulin protein complexes are considered distinct or functionally distinct where the recombinant immunoglobulin protein complexes have at least one different functional moiety. Thus, based on the type of one different functional moiety that is not shared by two recombinant immunoglobulin protein complexes, the recombinant immunoglobulin protein complexes may or may not have a shared function. For example, the pharmaceutical composition may include a first recombinant immunoglobulin protein complex that includes two functional moieties: an scFv binding to HER2 and a chemokine CXCL14 (e.g., two scFv binding to HER2 are coupled to two IL-15 binding domains (one scFv to one IL-15 binding domain) and two CXCL14 are coupled to two IL-15 (one CXCL14 to one IL-15); and a second recombinant immunoglobulin protein complex that includes two functional moieties: an scFv binding to a tumor neoepitope and an OX-40 ligand. In this example, two recombinant immunoglobulin protein complexes have no shared functional moieties, yet have a shared function: recognizing or targeting a tumor cell. In another example, the pharmaceutical composition may include a first recombinant immunoglobulin protein complex that includes two functional moieties: an scFv binding to HER2 and a chemokine CXCL14; a second recombinant immunoglobulin protein complex that includes two functional moieties: an scFv binding to HER2 and an OX-40 ligand. In this example, the first and second recombinant immunoglobulin protein complexes have a shared functional moiety (scFv binding to HER2), yet functionally distinct with two different functional moieties (CXCL14 and OX-40 ligand).

While the numbers and types of recombinant immunoglobulin protein complexes in such pharmaceutical composition requires at least two recombinant immunoglobulin protein complexes that are functionally distinct, it is preferred that the pharmaceutical composition includes at least three recombinant immunoglobulin protein complexes that are all functionally distinct from each other. Yet, it is also contemplated that where there are three or more than three recombinant immunoglobulin protein complexes in the pharmaceutical composition, at least two complexes are functionally distinct, and the rest of them share functions with at least one of the at least two complexes.

The plurality of recombinant immunoglobulin protein complexes can be further coupled to a carrier molecule including protein A, protein G, protein Z, albumin, refolded albumin, a nanoparticle (e.g., quantum dots, gold nanoparticles, magnetic nanoparticles, nanotubes, polymeric nanoparticles, dendrimers, etc.), or a bead (e.g., polystyrene bead, latex bead, dynabead, etc.). In some embodiments, the recombinant immunoglobulin protein complexes are coupled to different portions of the carrier molecule (e.g., Sudlow I and Sudlow II sites of albumin or refolded albumin, etc.) such that the carrier molecule can carry two recombinant immunoglobulin protein complexes independently from each other. In other embodiments, recombinant immunoglobulin protein complexes are coupled to the carrier molecule via an anchor molecule. In such embodiments, it is also contemplated that the anchor molecule includes a dendrimer-type linker to couple two recombinant immunoglobulin protein complexes independently or separately via two sublinkers (e.g., cleavable or non-cleavable).

In addition to CXCL14 as a functional moiety of the recombinant immunoglobulin protein complex, or as an alternative thereof, the pharmaceutical composition may also include one or more reagent upregulating endogenous CXCL-14 expression in a tumor cell. Exemplary reagents include some anti-cancer drug such as 5-aza-2'-deoxycytidine (decitabine or dacogen) or histone deacetylase (HDAC) inhibitor (e.g., trichostatin A, etc.). Alternatively, the pharmaceutical composition can be accompanied with a radiation therapy or chemotherapy that may increase CXCL-14 expression in a tumor cell.

In still another aspect of the inventive subject matter, the inventors contemplate that a pharmaceutical composition can be generated to include three elements: 1) a genetically-engineered engineered microorganism that includes or expresses tumor-associated antigen and a T-cell activating molecule, 2) a recombinant immunoglobulin protein complex having one or more functional moieties, and 3) a chemokine. Preferably, the microorganism is genetically engineered to express tumor-associated antigen and a T-cell activating molecule as two separate and distinct peptides. For example, the microorganism includes a recombinant nucleic acid having at least two nucleic acid segments (a sequence element): a first nucleic acid segment encoding a tumor-associated antigen and a second nucleic acid segment encoding a T-cell activating molecule in a single reading frame such that two nucleic acid segments can be translated into a single protein having two peptide segments under the same promoter. In this case, the inventors contemplate that the first and second nucleic acid segments are spaced with a spacer sequence (e.g., a nucleic acid sequence encoding a linker or a spacer of at least 10 amino acids, 15 amino acids, 20 amino acids, etc.). In other embodiments, the two nucleic acid segments may be transcribed separately into two distinct peptides. In still other embodiments, the two nucleic acid segments are present in the same reading frame, but separated by nucleic acid sequences encoding a type of 2A self-cleaving peptide (2A). As used herein, 2A self-cleaving peptide (2A) refers any peptide sequences that can provide a translational effect known as "stop-go" or "stop-carry" such that two sub-segments in the same mRNA fragments can be translated into two separate and distinct peptides. Any suitable types of 2A peptide sequences are contemplated, including porcine teschovirus-1 2A (P2A), thosea asigna virus 2A (T2A), equine rhinitis A virus 2A (E2A), foot and mouth disease virus 2A (F2A), cytoplasmic polyhedrosis virus (BmCPV 2A), and flacherie virus (BmIFV 2A).

It is especially preferred that the recombinant peptides encoded by the recombinant nucleic acid are expressed or present in the antigen presenting cells such that the antigen presenting cells expresses the tumor associated antigen and the T cell activating molecule on the surface to induce antigen-specific T cell activation. Thus, the recombinant nucleic acid is further placed in an expression vector to so deliver the recombinant nucleic acid to the antigen-presenting cells (e.g., dendritic cells, etc.), or to transcribe the nucleic acid sequence in bacteria or yeast so that the recombinant peptide encoded by the nucleic acid sequence can be, as a whole, or as fragments, delivered to the antigen presenting cell. Any suitable expression vectors that can be used to express protein are contemplated. Especially preferred expression vectors may include those that can carry a cassette size of at least 1 k, preferably 2 k, more preferably 5 k base pairs.

Thus, in one embodiment, the microorganism is a virus, and a preferred expression vector includes a viral vector (e.g., nonreplicating recombinant adenovirus genome, optionally with a deleted or non-functional E1 and/or E2b gene). In still further embodiments, the microorganism is a bacteria, and the expression vector can be a bacterial vector that can be expressed in a genetically-engineered bacterium, which expresses endotoxins at a level low enough not to cause an endotoxic response in human cells and/or insufficient to induce a CD-14 mediated sepsis when introduced to the human body. One exemplary bacteria strain with modified lipopolysaccharides includes ClearColi® BL21(DE3) electrocompetent cells. This bacteria strain is BL21 with a genotype F—ompT hsdSB (rB—mB—) gal dcm Ion λ(DE3 [lacI lacUV5-T7 gene 1 ind1 sam7 nin5])msbA148 ΔgutQΔkdsD ΔlpxLΔlpxMΔpagPΔlpxPΔeptA. In this context, it should be appreciated that several specific deletion mutations (ΔgutQ ΔkdsD ΔlpxL ΔlpxMΔpagPΔlpxPΔeptA) encode the modification of LPS to Lipid IVA, while one additional compensating mutation (msbA148) enables the cells to maintain viability in the presence of the LPS precursor lipid IVA. These mutations result in the deletion of the oligosaccharide chain from the LPS. More specifically, two of the six acyl chains are deleted. The six acyl chains of the LPS are the trigger which is recognized by the Toll-like receptor 4 (TLR4) in complex with myeloid differentiation factor 2 (MD-2), causing activation of NF-kB and production of proinflammatory cytokines. Lipid $IV_A$, which contains only four acyl chains, is not recognized by TLR4 and thus does not trigger the endotoxic response. While electrocompetent BL21 bacteria is provided as an example, the inventors contemplates that the genetically modified bacteria can be also chemically competent bacteria. Alternatively, or additionally, the microorganism is a yeast, and the expression vector can also be a yeast vector that can be expressed in yeast, preferably, in *Saccharomyces cerevisiae* (e.g., GI-400 series recombinant immunotherapeutic yeast strains, etc.).

The recombinant immunoglobulin protein complex in this pharmaceutical composition may include at least one functional moiety, preferably two moieties. While the functional moieties can be at least one of a binding motif to a tumor-associated antigen, a T cell activating molecule and/or a chemokine, it is preferred that at least one functional moiety is a binding motif to a tumor-associated antigen such that the recombinant immunoglobulin protein complex can be targeted to the tumor cells in the tumor microenvironment. In some embodiments, the tumor-associated antigen targeted by the recombinant immunoglobulin protein complex may be same with the tumor-associated antigen that is expressed in the antigen presenting cells by the genetically-engineered microorganism. In other embodiments, the tumor-associated antigen targeted by the recombinant immunoglobulin protein complex may be different from the tumor-associated antigen that is expressed in the antigen presenting cells by the genetically-engineered microorganism. For example, the tumor-associated antigen targeted by the recombinant immunoglobulin protein complex can be a tumor-specific, patient-specific neoepitope, while the tumor-associated antigen that is expressed in the antigen presenting cells is HER2.

It is further contemplated that the pharmaceutical composition includes an immune stimulatory cytokine (e.g., IL-2, IL-8, etc.) and a chemokine (e.g., CXCL14, CD40L, CCL2, CCL1, CCL22, CCL17, CXCR3, CXCL9, CXCL10, CXCL11, CXCL14, etc.), which can attract immune competent cells (e.g., T cells, B cells, NK cells, NKT cells, dendritic cells, macrophage etc.) to the tumor microenvironment and/or activate the immune competent cells. In some embodiments, the immune stimulatory cytokine or a chemokine can be coupled with the recombinant immunoglobulin protein complex. In other embodiment, the immune stimulatory cytokine or a chemokine can be coupled with the recombinant immunoglobulin protein complex can be coupled to the surface of the genetically-modified microorganism via a cleavable linker (e.g., acid-labile linker). In such embodiments, the linker can be conjugated to the N-hydroxysuccinimidyl-PEG (PEG-NETS), by which the linker covalently bonds with all kinds of membrane proteins having amino groups on cell surfaces. Alternatively, the linker can be conjugated with PEG to form PEG-glycolipid or with poly(vinyl alcohol) carrying alkyl side chains (PVA-alkyl) such that the conjugated linker can anchor to the membrane lipid bilayer of the genetically modified microorganism (e.g., virus) through hydrophobic interactions. In still other embodiments, the immune stimulatory cytokine or a chemokine can be present in the pharmaceutical composition as a distinct molecule (not directly coupled to the recombinant immunoglobulin protein complex).

Additionally, where the chemokine is coupled to the surface of genetically-engineered microorganism, it is also contemplated that the recombinant immunoglobulin protein complex can be also coupled to the surface of the genetically-engineered microorganism. In this embodiment, it is preferred that the recombinant immunoglobulin protein complex and the chemokine are coupled to the genetically-engineered microorganism via cleavable linker, preferably acid-labile linker such that the recombinant immunoglobulin protein complex and chemokine can be separated from the genetically engineered organism once the complex (genetically-engineered microorganism with recombinant immunoglobulin protein complex and chemokine) is placed in the acidic tumor microenvironment. Alternatively, the pharmaceutical composition having three elements as described above is further coupled to a carrier protein (e.g., protein A, protein G, protein Z, albumin, refolded albumin) via a linker (cleavable or non-cleavable) such that all elements can be targeted to the tumor microenvironment together.

Such generated recombinant immunoglobulin protein complex and/or pharmaceutical compositions that includes recombinant immunoglobulin protein complex(es) can be formulated in any pharmaceutically acceptable carrier (e.g., as a sterile injectable composition) and administered to a patient having a tumor to increase effectiveness of immune therapy to so treat the tumor (e.g., to modulate (e.g., reduce, abrogate, etc.) immune suppression by the tumor, to reduce the tumor size, etc.). In some embodiments, the recombinant immunoglobulin protein complex and/or pharmaceutical compositions can be administered via systemic injection including subcutaneous, subdermal injection, or intravenous injection. In other embodiments, where the systemic injection may not be efficient (e.g., for brain tumors, etc.) or more localized treatment is desired, it is contemplated that the recombinant immunoglobulin protein complex and/or pharmaceutical compositions can be administered via intratumoral injection. As used herein, the term "administering" refers to both direct and indirect administration of the compounds and compositions contemplated herein, where direct administration is typically performed by a health care professional (e.g., physician, nurse, etc.), while indirect administration typically includes a step of providing or making the compounds and compositions available to the health care professional for direct administration.

With respect to dose and schedule of the formulation administration, it is contemplated that the dose and/or schedule may vary depending on the type of protein, protein complex, or the type of the pharmaceutical composition (e.g., virus, bacteria, yeast, in combination with recombinant protein complex, etc.), a type and prognosis of disease (e.g., tumor type, size, location), health status of the patient (e.g., including age, gender, etc.). While it may vary, the dose and schedule may be selected and regulated so that the formulation does not provide any significant toxic effect to the host normal cells, yet sufficient to be reduce immune suppression by reduced CXCL-14 expression or presence in the tumor microenvironment. Thus, in a preferred embodiment, an optimal or desired condition of administering the formulation can be determined based on a predetermined threshold. For example, the predetermined threshold may be a predetermined local or systemic concentration of CXCL-14 in the tumor microenvironment. Therefore, administration conditions are typically adjusted to have CXCL-14 increased in the tumor microenvironment at least 20%, at least 30%, at least 50%, at least 60%, at least 70% at least for 24 hours, 48 hours, 72 hours, 7 days, etc. In another example, the predetermined threshold may be a predetermined local or systemic concentration of cytokine (e.g., IFN-γ, IL-10, IL-13, etc.) released from activated NK cells or concentration of T cell activating cytokines (e.g., IL-12, IL-23, IL-1b, IL-6, TGF-β, etc.) that are expressed by T cells upon interaction of antigen presenting cells to differentiate into subset of activated T cells. Therefore, administration conditions are typically adjusted to have the concentration of cytokine increased at least 20%, at least 30%, at least 50%, at least 60%, at least 70% at least locally or systemically. Moreover, it is contemplated that the compounds and compositions presented herein may be co-administered (contemporaneously or sequentially) with NK cells. For example, suitable NK cells include autologous NK cells as well as NK92 cells and derivatives thereof (e.g., aNK cells, haNK cells, taNK cells, al commercially available from NantKwest, 9920 Jefferson Blvd. Culver City, CA 90232).

Without wishing to be bound by any specific theory, the inventors contemplate that administration of pharmaceutical composition (the recombinant immunoglobulin protein complex, a recombinant protein complex having a carrier protein, a plurality of recombinant protein complex associated with a carrier, a pharmaceutical composition having a genetically-engineered microorganism and a recombinant protein complex, etc.) to a patient is expected to cause the delivery of the pharmaceutical composition in a tumor microenvironment, preferably by targeting a tumor cell. When the composition is delivered, it is expected that multiple functional moieties of the composition will provide distinct but complementary or even synergistic effect to the tumor microenvironment. For example, where the recombinant protein complex having three functional moieties, 1) a binding motif to a tumor-associated antigen, 2) a T-cell activating molecule, and 3) a chemokine coupled to TxM backbone, it is expected that the recombinant protein complex will target the tumor microenvironment via binding to the tumor-associated antigen expressed on the tumor cell. In the tumor microenvironment, the chemokine (e.g., CXCL14) will increase the infiltration of immune competent cells including dendritic cells, and the T cell activating molecule (e.g., OX-40 ligand) will induce T cell activation by binding to T cell receptor (OX-40) and mimicking dendritic cell-T cell interaction. In addition, the presence of the IL-15 or IL-15 superagonist will advantageously attract and activate T cells and NK cells, while the presence of the Fc portion facilitates ADCC. Thus, in this example, administration of the recombinant protein complex can not only overcome the suppression of antitumor immune response by downregulation of CXCL14, but also further boost the antitumor immune response by attracting and activating immune competent cells in the tumor microenvironment. The inventors contemplate that similar combinatorial effect can be obtained by administering a pharmaceutical composition that has a plurality of recombinant protein complexes, which, in combination, introduce a binding motif to a tumor-associated antigen, a T-cell activating molecule, a chemokine, IL-15 superagonist, and Fc domains.

In another example, where the pharmaceutical composition includes a genetically-engineered microorganism including a tumor-associated antigen and a T-cell activating molecule, a recombinant immunoglobulin protein complex with a functional moiety, and chemokine, it is expected that the pharmaceutical composition will be target the tumor microenvironment by binding to the tumor-associated antigen expressed on the tumor cell. Where the genetically-engineered microorganism is a virus, the virus will infect the antigen presenting cells to so produce the tumor-associated antigen and the T-cell activating molecule in the antigen presenting cells. Presentation of tumor-associated antigen and the T-cell activating molecule (e.g., OX-40 ligand) will induce activation of T cells that are tumor-associated antigen-specific (recognizing tumor-associated antigen) by binding to T cell receptor (OX-40). In addition, release of chemokine (e.g., CXCL14) will increase the infiltration of immune competent cells including dendritic cells, and the presence of the IL-15 or IL-15 superagonist in the recombinant immunoglobulin protein complex will advantageously attract and activate T cells and NK cells, while the presence of the Fc portion in the recombinant immunoglobulin protein complex will facilitates ADCC.

Thus, it should be appreciated that the compositions and methods presented herein can provide more effective treatment using multiple anti-tumor compounds by specifically targeting the multiple compounds to the tumor microenvironment and concurrently delivering of the compounds to a small target area such that the amount and the type of multiple anti-tumor compounds can be co-controlled. It is expected that such concurrent and targeted delivery of multiple anti-tumor compounds would synergize the effects of multiple anti-tumor compounds compared to individual delivery of the anti-tumor compounds, where the delivery timing, location, and effect of the individual anti-tumor compound may vary. Further, such approach would also provide an effective focal treatment to some tumor cells that are affected by specific tumor-associated pathway. For example, EGFR overexpression in the tumor cell may downregulate CXCL14 expression that results in increased immune resistance of the tumor cells. Thus, targeted delivery of CXCL14 and other immune activating molecules (e.g., OX-40 ligands, etc.) to the tumor environment with EGFR binding motif as a functional moiety of the protein complex can reverse immune resistance of the tumor cells overexpressing EGFR.

In addition, the inventors contemplate that the compositions presented herein, especially the recombinant immunoglobulin protein complex can mimic the function of antigen presenting cells by binding to the tumor cells expressing a tumor-associated molecules via a binding motif to the tumor-associated antigen. Once bound to the tumor-associated molecule on the surface of the tumor cell, the recombinant immunoglobulin protein complex can activate T cell-mediated immune response against the tumor cells via T-cell activating molecule (e.g., OX-40 ligand) associated with recombinant immunoglobulin protein complex. Optionally, release of chemokine (e.g., CXCL14) from recombinant immunoglobulin protein complex will increase the infiltration of immune competent cells to further boost the immune response. Thus, the recombinant immunoglobulin protein complex acts like a dendritic cells (like an avatar) expressing tumor associated molecule on its surface to induce immune response against the tumor cell. Consequently, such activation of immune system may revert the immune-suppressive environment of tumor microenvironment to immune-active environment, which can be especially beneficial to treat a patient having an immune-suppressed tumor.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

What is claimed is:

1. A recombinant immunoglobulin protein complex, comprising:
   an Fc domain having first and second Fc portions coupled with respective first and second cytokine binding domains having respective first and second functional moieties, wherein the first and second cytokine binding domains are IL-15Rα;
   a first cytokine coupled with a third functional moiety and a second cytokine coupled with a fourth functional moiety, wherein first and second cytokines are IL-15;
   wherein the first cytokine binding domain is coupled with the first cytokine and the second cytokine binding domain is coupled with the second cytokine;
   wherein at least two of the first, second, third, and fourth functional moieties are functionally distinct, and the first, second, third, and fourth functional moieties are selected from a group consisting of a T-cell activating molecule, a chemokine, and an anti-tumor-associated antigen binding motif; and
   wherein the T-cell activating molecule is 4-1BB ligand, wherein the chemokine is CXCL-14, and wherein the tumor associated antigen is HER2.

2. The protein complex of claim 1, wherein the first and second Fc portions form a dimer.

3. The protein complex of claim 1, further comprising a fifth functional moiety that is coupled to N-terminus of at least one of the first and second Fc portions via a linker.

4. The protein complex of claim 3, wherein the linker is an acid-labile linker.

5. The protein complex of claim 1, further comprising a fifth functional moiety that is coupled to at least one of the first cytokine binding domain or the first cytokine via a linker.

6. The protein complex of claim 5, wherein the fifth functional moiety and the first functional moiety are coupled to the first cytokine binding domain, wherein the linker comprises first and second sublinkers, wherein the first sublinker is coupled to the first functional moiety and the second sublinker is coupled to the fifth functional moiety, and wherein at least one of the sublinkers is an acid-labile linker.

7. The protein complex of claim 1, wherein the protein complex is coupled with a carrier protein via the Fc domain, and wherein the carrier protein is selected from the following: protein A, protein G, protein Z, albumin, refolded albumin.

8. A pharmaceutical composition comprising:
   a plurality of recombinant immunoglobulin protein complexes, each of the recombinant immunoglobulin protein complexes comprising:
   an Fc domain having first and second Fc portions coupled with respective first and second cytokine binding domains having respective first and second functional moieties, wherein the first and second cytokine binding domains are IL-15Rα;
   a first and a second cytokine coupled with a third and a fourth functional moieties, respectively, wherein first and second cytokines are IL-15;
   wherein the first and second cytokine binding domains are coupled with the first and second cytokines, respectively;
   wherein at least two of the first, second, third, and fourth functional moieties are functionally distinct, and the first, second, third, and fourth functional moieties are selected from a group consisting of a binding motif to a tumor-associated antigen, a T-cell activating molecule, and a chemokine; and
   wherein the T-cell activating molecule is 4-1BB ligand, wherein the chemokine is CXCL-14, and wherein the tumor associated antigen is HER2.

9. The composition of claim 8, wherein the first and second Fc portions form a dimer.

10. The composition of claim 8, wherein the protein complexes are coupled with a carrier protein via the Fc domain, and wherein the carrier protein is selected from the following: protein A, protein G, protein Z, albumin, refolded albumin.

11. The composition of claim 8, further comprising a fifth functional moiety that is coupled to N-terminus of at least one of the first and second Fc portions via a linker.

12. The protein complex of claim 11, wherein the linker is an acid-labile linker.

13. The composition of claim 8, further comprising a fifth functional moiety that is coupled to at least one of the first cytokine binding domain or the first cytokine via a linker.

14. The composition of claim 13, wherein the fifth functional moiety and the first functional moiety are coupled to the first cytokine binding domain, wherein the linker comprises first and second sublinkers, wherein the first sublinker is coupled to the first functional moiety and the second sublinker is coupled to the fifth functional moiety, and wherein at least one of the sublinkers is an acid-labile linker.

15. The composition of claim 8, formulated for injection.

16. The composition of claim 15, wherein the injection is subcutaneous, subdermal injection, or intravenous injection.

17. The composition of claim 8, wherein the plurality of cells are NK cells.

* * * * *